United States Patent
Wenc

(10) Patent No.: US 8,640,643 B2
(45) Date of Patent: Feb. 4, 2014

(54) METHOD FOR CONTROLLING DRUG LOADING IN A MEDICAL DEVICE

(75) Inventor: Kate Elaine Wenc, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 825 days.

(21) Appl. No.: 12/643,624

(22) Filed: Dec. 21, 2009

(65) Prior Publication Data

US 2010/0166941 A1 Jul. 1, 2010

Related U.S. Application Data

(60) Provisional application No. 61/140,916, filed on Dec. 26, 2008.

(51) Int. Cl.
*B05C 13/02* (2006.01)
*B05C 13/00* (2006.01)

(52) U.S. Cl.
USPC .......................................... 118/503; 118/500

(58) Field of Classification Search
None
See application file for complete search history.

(56) References Cited

U.S. PATENT DOCUMENTS

| | | | |
|---|---|---|---|
| 3,893,843 A | 7/1975 | Fry et al. | |
| 4,001,460 A | 1/1977 | Kinney et al. | |
| 4,308,363 A | 12/1981 | Vaughn | |
| 4,710,233 A | 12/1987 | Hohmann et al. | |
| 5,188,670 A | 2/1993 | Constantz | |
| 5,217,493 A | 6/1993 | Raad et al. | |
| 5,505,218 A | 4/1996 | Steinhauser et al. | |
| 5,624,704 A | 4/1997 | Darouiche et al. | |
| 5,756,145 A | 5/1998 | Darouiche | |
| 5,851,485 A | 12/1998 | Lin et al. | |
| 5,853,745 A | 12/1998 | Darouiche | |
| 5,871,692 A | 2/1999 | Haire et al. | |
| 5,902,283 A | 5/1999 | Darouiche et al. | |
| 6,001,425 A | 12/1999 | Stash et al. | |
| 6,129,928 A | 10/2000 | Sarangapani et al. | |
| 6,162,487 A | 12/2000 | Darouiche | |
| 6,254,921 B1 | 7/2001 | Chappa et al. | |
| 6,534,112 B1 | 3/2003 | Bouchier et al. | |
| 6,916,377 B2 | 7/2005 | Bouchier et al. | |
| 2006/0041091 A1* | 2/2006 | Chang et al. | 526/247 |
| 2006/0161253 A1* | 7/2006 | Lesh | 623/8 |
| 2008/0208325 A1* | 8/2008 | Helmus et al. | 623/1.44 |
| 2009/0076591 A1* | 3/2009 | Girton et al. | 623/1.16 |
| 2009/0148492 A1* | 6/2009 | Dave et al. | 424/423 |
| 2009/0171388 A1* | 7/2009 | Dave et al. | 606/213 |

OTHER PUBLICATIONS

Raad et al., "Central Venous Catheters Coated with Minocycline and Rifampin for the Prevention of Catheter-Related Colonization and Bloodstream Infections", *Annals of Internal Medicine*, vol. 127, No. 4, Aug. 15, 1997, pp. 267-274.

Raad et al., "Antibiotics and Prevention of Microbial Colonization of Catheters", *Antimicrobial Agents and Chemotherapy*, vol. 39, No. 11, Nov. 1995, pp. 2397-2400.

* cited by examiner

*Primary Examiner* — Dah-Wei Yuan
*Assistant Examiner* — Jethro Pence
(74) *Attorney, Agent, or Firm* — Kagan Binder, PLLC

(57) ABSTRACT

Systems and relative methods for regulating the loading capacity of a coating sleeve affixed to an outer surface of an implantable medical device to control an amount of antimicrobial agent delivered with the implantable medical device. A coating sleeve defines fibril void spaces into which therapeutic agents are loaded. A clamp is positioned on the coating sleeve to adjust the volume of the fibril void spaces so as to regulate the loading capacity of the coating sleeve.

12 Claims, 1 Drawing Sheet

METHOD FOR CONTROLLING DRUG LOADING IN A MEDICAL DEVICE

PRIORITY CLAIM

The present application claims priority to U.S. Provisional Application Ser. No. 61/140,916, filed Dec. 26, 2008, and entitled "METHOD FOR CONTROLLING DRUG LOADING IN A MEDICAL DEVICE," which is herein incorporated by reference in its entirety.

FIELD OF THE INVENTION

The present invention relates generally to implantable medical devices loaded with an antimicrobial agent. More specifically, the present invention relates to selectively adjusting the loading capacity of the implantable medical device through physical manipulation of a sleeve covering the implantable medical device to increase or decrease an amount of fibril void space in the sleeve that is capable of receiving an antibacterial agent.

BACKGROUND OF THE INVENTION

Localized and systemic infections represent one of the most serious post surgical complications. Over the past fifty years tremendous advances in materials, training and antimicrobial therapies have significantly reduced the number of life-threatening post operative infections. The development of pre-sterilized disposable surgical dressings, medical instruments, gowns, drapes and other materials have helped reduce infection frequency. However, the development of improved antimicrobials represents the single most significant advance in infection control.

Deep tissue infections can result when medical implants become contaminated prior to or during surgical placement. When oral or parenterally administered antimicrobials fail to effectively control and eliminate the infection, the medical implant may have to be removed. Removal requires additional surgical procedures to treat the infection as well as to re-implant the device after the infection completely resolves. Moreover, once deep tissue infections are established, long term antimicrobial therapy and hospitalization may be required. These additional procedures increase the costs associated with device implantation, subject the patient to discomfort and in rare circumstances can result in severe long term health issues such as, increasing the threat of permanent disfigurement.

Coating implantable medical devices with antimicrobial compounds allows for deep tissue drug delivery that can significantly reduce the risk of post implantation infections. Coating procedures should employ broad spectrum antimicrobials that are effective against most post surgical infections, especially MRSA (multiple-resistant *Staphylococcus aureus*) infections. The antimicrobials must be soluble in physiological fluids and stable enough to survive processing steps required to successfully coat the medical device. Ideally, a synergistic antimicrobial combination should be used. In addition, the size, shape and composition of the medical devices can significantly impact the success of the coating procedure.

One representative example of an implantable medical device coated with antimicrobial compounds include INHIBIZONE treatment products developed and sold by American Medical Systems of Minnetonka, Minn. These products generally include an implantable medical device such as, for example, components comprising a penile implant such as the AMS 700™ Series that have been coated with a combination of rifampin and minocycline using the processes and systems as disclosed in U.S. Pat. Nos. 6,534,112 and 6,916,377, which are herein incorporated by reference. The INHIBIZONE coating is readily dissolved when exposed to the warm, moist conditions found within the body such that the instances of infection are significantly reduced.

While, the INHIBIZONE treatment products are successful in reducing the occurrence of infection with implantable medical devices, it would be advantageous to further improve upon the coating process so as to more precisely control loading of the implantable medical device with the antimicrobial agent.

SUMMARY OF THE INVENTION

The present disclosure relates to systems and methods of regulating the coating of implantable medical devices with antimicrobial agents. Specifically, the present invention discloses systems and methods for controlling the characteristics of the antimicrobial coating of implantable medical devices by manipulating the loading of antimicrobial agent into a coating medium affixed to the outer surface of the implantable medical device.

It is an object of the present invention to provide systems and methods for regulating the loading of antimicrobial agents into a coating medium for the coating of a medical device. The present invention also provides systems and methods for applying reproducible coatings to medical devices by providing means for adjusting the amount of antimicrobial agents loadable into the coating medium to create coatings with more consistent characteristics.

In one aspect, the present disclosure is directed at a system for loading a coating medium affixed to an implantable medical device with antimicrobial agents. Typically, the coating medium is loosely affixed to the outer surface of the implantable medical device. An antimicrobial treatment is then applied to the outside surface of the coating medium. The antimicrobial agents are loaded into the coating medium by diffusing into a network of fibril void spaces within the coating medium. The coating medium is then treated again to form a coating on the implantable medical device. The loading capacity of the coating medium for antimicrobial agents directly affects the characteristics of the coating as the amount of antimicrobial agents loaded into the coating medium will change the characteristics of the coating. The present disclosure is directed to a system for controlling the loading capacity of the coating medium to control the characteristics of the coating formed on the surface of the implantable medical device.

In another aspect, the present disclosure is directed at a system for producing reproducible coatings on implantable medical devices by controlling the loading capacity of the coating sleeve. Specifically, the disclosure is directed at a system and method of manipulating the volume of the fibril void spaces within the coating medium to control the loading capacity of various portions of the coating sleeve to load different amounts of antimicrobial agents into the various regions.

In another aspect, the present invention is directed at a system for creating different coating regions on the outer surface of the implantable medical device. Specifically the disclosure is directed at a system and method for manipulating the coating medium wherein different regions of the coating medium have different fibril void space volumes. The differing fibril void space volumes of the various regions will ultimately cause coating regions with different coating characteristics on the implantable medical device.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follow more particularly exemplify these embodiments.

BRIEF DESCRIPTION OF THE DRAWINGS

The invention may be completely understood in consideration of the following detailed description of various embodiments of the invention in connection with the accompanying drawings, in which.

Figure 1:
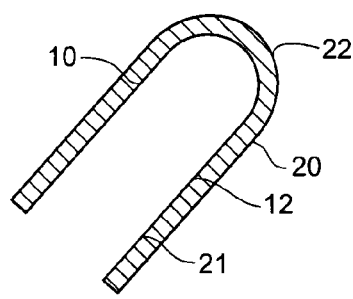
FIG. 1 is a partial cross-sectional view of an implantable medical device with a coating sleeve affixed and in a neutral state.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

As illustrated in FIG. 1, a representative embodiment of an implantable medical device 10 according to the present disclosure is covered by a coating sleeve 20. The implantable medical device 10 further comprises an outer surface 12 over which the coating sleeve 20 is positioned. The coating sleeve 20 further comprises an inner surface 21 in operational contact with the implantable medical device's 10 outer surface 12 and a coating sleeve outer surface 22 treatable with an antimicrobial agent solution.

Figure 2:
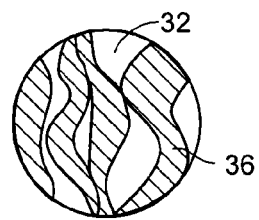
FIG. 2 is a detailed view of a portion of a coating sleeve wherein the fibril void spaces are in a neutral state of expansion.

As shown in FIG. 2, the coating sleeve 20 provides a coating medium for the implantable medical device 10 and comprises a fibrous material having solid nodes 36 and fibril void spaces 32. An antimicrobial solution applied to the outer surface 22 of the coating sleeve 20 diffuses into the fibril void spaces 32 of the coating sleeve 20. The volume of the fibril void spaces 32 defines the volume of antimicrobial agent that may be loaded into the coating sleeve 20. In other words, the volume of the fibril void spaces 32 defines the capacity of the coating sleeve 20 for an antimicrobial agent.

Figure 3:
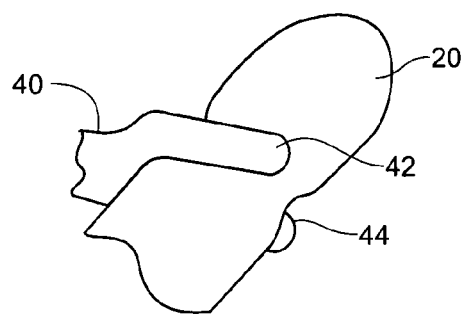
FIG. 3 is a perspective view of an implantable medical device with a coating sleeve affixed and a clamp compressing a region of the coating sleeve against an outer surface of the implantable medical device.
Figure 4:
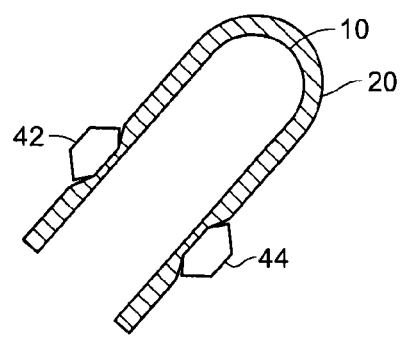
FIG. 4 is a partial cross-sectional view of an implantable medical device with a coating sleeve affixed and a clamp compressing a region of the sleeve against an outer surface of the implantable medical device.

As illustrated in FIG. 3, a representative embodiment of the present invention also comprises a clamp 40 for compressing the coating sleeve 20. The clamp 40 further comprises a first fork 42 and a second fork 44 that cooperatively compress a portion of the coating sleeve 20 against the implantable medical device 10. Clamp 40 can comprise a variety of suitable clamp designs including, for example, a bulldog clamp available from World Precision Instruments of Sarasota, Fla. or a clip available from Qosina Company of Edgewood, N.J.

Figure 5:
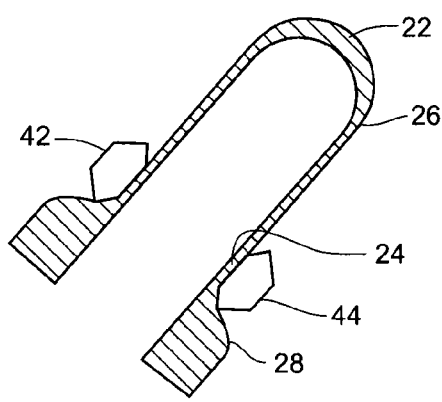
FIG. 5 is a partial cross-sectional view of an implantable medical device with a coating sleeve affixed where a clamp has been shifted to compress a first portion of the sleeve and to stretch a second portion of the sleeve.

As illustrated in FIG. 5, the clamp 40 can be moved along the length of the implantable medical device 10 while maintaining a compression grip on the coating sleeve 20. Shifting the clamp 40 along the length of the implantable medical device's 10 will compress a portion of the coating sleeve 20 creating a compressed region 28 and similarly will stretch a portion of the coating sleeve 20 creating a stretched region 26.

Figure 6:
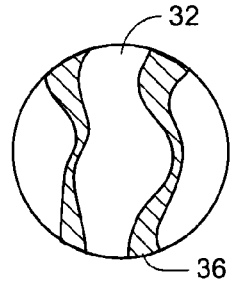
FIG. 6 is a detailed view of a portion of a coating sleeve wherein fibril void spaces are in a stretched state of expansion.
Figure 7:
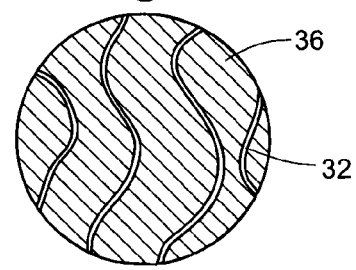
FIG. 7 is a detailed view of a portion of a coating sleeve wherein fibril void spaces are in a compressed state of expansion.

As illustrated in FIGS. 6-7, shifting the clamp 40 causes fibril void spaces 32 in the compressed region 28 to close reducing the loading capacity of the coating sleeve 20 for antimicrobial agents in the compressed region 28. The low loading capacity of the compressed region 28 will result in a lightly coated or uncoated portion of the outer surface 12 of the implantable medical device 10. Similarly, shifting the clamp 40 causes the fibril void spaces 32 to expand in the stretched region 26 increasing the loading capacity of the coating sleeve 20 in the stretched region 26. The increased loading capacity of the stretched region 26 will result in a more heavily coated region on the outer surface 12 of the implantable medical device.

By employing the clamp 40 to control the volume of the fibril void spaces 32 in various regions of the coating sleeve 20, the characteristics of the coating on the outer surface 12 of the implantable medical device 10 may be controlled. Control of the antimicrobial agent coating on the implantable medical device 10 has a number of advantages. For example, different regions of the implantable medical device 10 that cross multiple types of tissue may be coated with different antimicrobial agents to cope with the particular tissue that that particular region of the implantable medical device 10 is in. Also, as "pot life" or the shelf life of the antimicrobial coating before implantation is a constant concern, the clamping method may be used to "lock" the implantable medical device 10 by closing all of the fibril void spaces 32 until the implantable medical device 10 is implanted.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

The invention claimed is:

1. A system for loading a coating agent onto an implantable medical device, the system comprising:
   an implantable medical device having an outer device surface,
   a coating sleeve comprising a sleeve outer surface, a sleeve inner surface, and a sleeve wall disposed between the sleeve outer surface and the sleeve inner surface, the coating sleeve disposed over the outer device surface with the sleeve inner surface placed against the outer device surface, the coating sleeve defining fibril void spaces in the sleeve wall between the sleeve outer surface and the sleeve inner surface, the fibril void spaces adapted to receive an amount of a coating agent, wherein the amount of coating agent receivable by the fibril void spaces corresponds to fibril void volume defined by the fibril void spaces; and a clamp adapted for placement on the coating sleeve while the coating sleeve is disposed over the outer device surface with the sleeve inner surface placed against the outer device surface such that the clamp contacts the sleeve outer surface to mechanically manipulate the fibril void volume between the sleeve outer surface and the sleeve inner surface.

2. The system of claim 1, wherein the coating agent is an antimicrobial agent.

3. The system of claim 1, wherein the clamp defines a first coating region of the coating sleeve with first fibril void spaces having a first volume and a second coating region of the coating sleeve with the second fibril void spaces having a second volume.

4. The system of claim 3, wherein the first fibril void spaces are capable of receiving a first amount of the coating agent and the second fibril void spaces are capable of receiving a second amount of the coating agent.

5. The system of claim 1, wherein the clamp is adapted for placement on the coating sleeve while the coating sleeve is disposed over the outer device surface with the sleeve inner surface placed against the outer device surface, such that the clamp contacts the sleeve outer surface to mechanically manipulate the fibril void volume by compressing the sleeve wall.

6. The system of claim 1, wherein the clamp is adapted for placement on the coating sleeve while the coating sleeve is disposed over the outer device surface with the sleeve inner surface placed against the outer device surface, such that the clamp contacts the sleeve outer surface to mechanically manipulate the fibril void volume by compressing the sleeve wall and the clamp is capable of movement along a length of the coating sleeve while maintaining a compression grip on the coating sleeve to create a compressed region.

7. The system of claim 3, wherein the first fibril void spaces contain a first antimicrobial agent and the second fibril void spaces contain a second antimicrobial agent.

8. A method for controlling the loading of coating agent onto an implantable medical device, the method comprising providing a system comprising:

an implantable medical device having an outer device surface, a coating sleeve comprising a sleeve outer surface, a sleeve inner surface, and a sleeve wall disposed between the sleeve outer surface and the sleeve inner surface, the coating sleeve disposed over the outer device surface with the sleeve inner surface placed against the outer device surface, the coating sleeve defining fibril void spaces in the sleeve wall between the sleeve outer surface and the sleeve inner surface, the fibril void spaces adapted to receive an amount of a coating agent, wherein the amount of coating agent receivable by the fibril void spaces corresponds to fibril void volume defined by the fibril void spaces;

a clamp adapted for placement on the coating sleeve while the coating sleeve is disposed over the outer device surface with the sleeve inner surface placed against the outer device surface such that the clamp contacts the sleeve outer surface to mechanically manipulate the fibril void volume between the sleeve outer surface and the sleeve inner surface, disposing the coating sleeve over the outer device surface with the sleeve inner surface placed against the outer device surface, and applying the clamp to the coating sleeve to vary sizes of the fibril void spaces.

9. A method as recited at claim 8 comprising moving the clamp along a length of the coating sleeve to create a compressed region.

10. A method as recited at claim 8 comprising maintaining the position of the clamp on the coating sleeve to close fibril void spaces to lengthen a pot life of the antimicrobial agent.

11. A method as recited at claim 8 wherein the step of applying the clamp to the coating sleeve comprises defining a first coating region of the coating sleeve having first fibril voids spaces having a first volume; and defining a second coating region of the coating sleeve having first fibril voids spaces having a first volume.

12. A method as recited at claim 11 comprising manipulating the position of the clamp along the coating sleeve to change the size of the first fibril void spaces and the second fibril void spaces.

* * * * *